US00PP15753P2

(12) United States Plant Patent
Lim et al.

(10) Patent No.: US PP15,753 P2
(45) Date of Patent: May 3, 2005

(54) SHRUB ROSE PLANT NAMED 'BAIFACE'

(50) Latin Name: *Rosa hybrida*
Varietal Denomination: BAIface

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 46 days.

(21) Appl. No.: 10/796,100

(22) Filed: Mar. 10, 2004

(51) Int. Cl.[7] ..... A01H 5/00
(52) U.S. Cl. ..... Plt./102
(58) Field of Search ..... Plt./102

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which forms on a continuous basis in clusters attractive semi-double rich medium pink blossoms blended with rosy pink and white. The plant exhibits a compact, upright and bushy growth habit, satiny medium green foliage, and excellent tolerance to Black Spot and Powdery Mildew. The attractive medium green foliage contrasts nicely with the pink blossom coloration. A tough rose plant of good hardiness is provided. The plant can be grown to advantage as a specimen, border planting, or as a mass planting.

1 Drawing Sheet

Botanical commercial classification: *Rosa hybrida*/Shrub Rose Plant.
Varietal denomination: cv. 'BAIface'.

SUMMARY OF THE INVENTION

The new variety of *Rosa hybrida* landscape shrub rose plant was created at Yamhill, Oreg. during 1993 by artificial pollination wherein two parents were crossed which previously had been studied in the hope that they would contribute the desired characteristics. The female parent (i.e., the seed parent) was the 'Earth Song' variety (non-patented in the United States). The male parent (i.e., the pollen parent) was the 'Meipoque' variety (U.S. Plant Pat. No. 5,956). The 'Meipoque' variety is marketed under the PINK MEIDILAND trademark. The parentage of the new variety can be summarized as follows:

'Earth Song'×'Meipoque'.

The seeds resulting from the above pollination were sown and plants were obtained which were physically and biologically different from each other. Selective study resulted in the identification during 1996 of a single plant of the new variety having the distinctive ornamental characteristics hereafter described.

It was found that the new variety of the present invention:

(a) exhibits a compact, upright and bushy growth habit, (b) forms continuously in clusters attractive semi-double rich medium pink blossoms blended with rosy pink and white, (c) forms satiny medium green adult foliage, (d) displays excellent tolerance to Black Spot and Powdery Mildew; and (e) is particularly well suited for growing as attractive ornamentation in parks and gardens.

The red-purple buds open to rich medium pink blooms having a blend of rosy pink and white that lightens in coloration with maturity. The blossom coloration contrasts nicely with the medium green adult foliage. A tough shrub rose plant having good hardiness is provided.

The new variety well meets the needs of the horticultural industry. It can be grown to advantage anywhere in the landscape where attractive ornamentation is desired. The distinctive blossoms are displayed throughout the summer on a continuous basis. The plant can be grown as a specimen, border planting, or as a mass ground cover.

The new variety can be readily distinguished from its parental varieties. More specifically, the 'Earth Song' variety is a Grandiflora rose that forms Tyrian red blossoms having considerably more petals, and the 'Meipoque' variety forms clear pink blossoms with a white center having only five petals.

The new variety also can be readily distinguished from the 'Nearly Wild' variety (non-patented in the United States) and the 'Meipitac' variety (U.S. Plant Pat. No. 7,783). More specifically, the 'Nearly Wild' plant commonly assumes a lesser height of approximately 80 cm, and forms single blossoms having only five petals that are medium rose pink on the obverse and light pink on the reverse. The 'Meipitac' plant commonly is taller and assumes a height of approximately 1 m, and forms smaller double blossoms having approximately 24 petals that are medium pink blended with light pink on the obverse and light pink on the reverse.

The new variety has been found to undergo asexual propagation by budding on an understock beginning in August 1994 and by the rooting of cuttings. 'Dr. Huey' rootstock was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated 99R513. The new variety subsequently has been named the 'BAIface' variety, and currently is being marketed while using the GARDEN JUBILEE and FUNNY FACE trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn. during the 2002.

DETAILED DESCRIPTION

Figure 1:
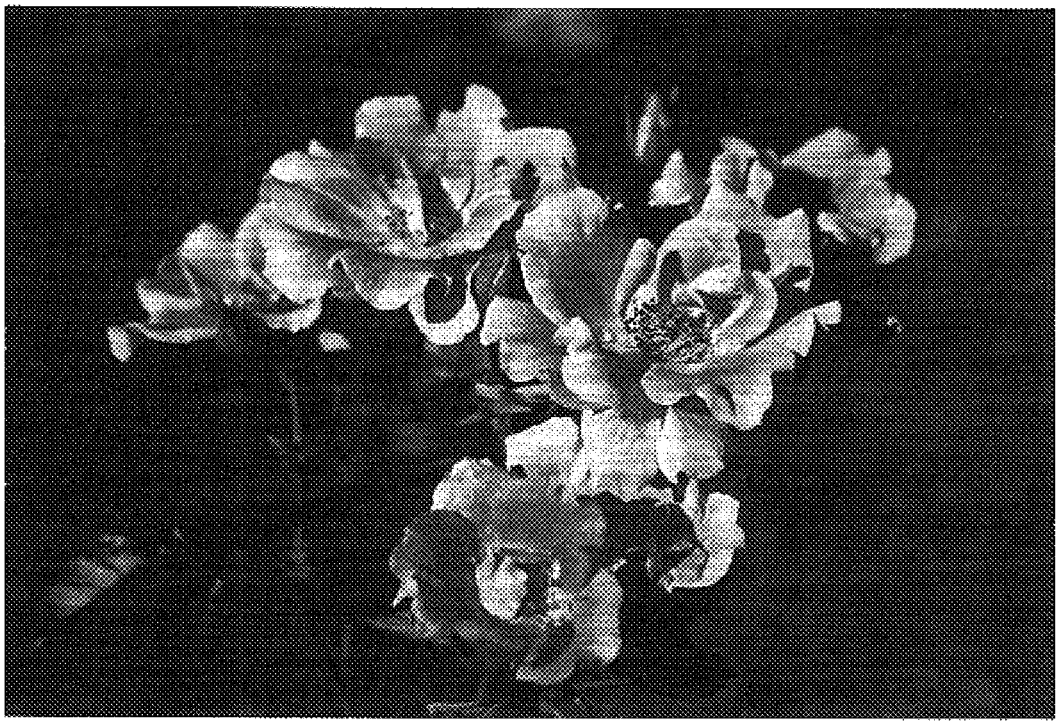
FIG. 1 illustrates typical blossom clusters and foliage of the new variety. The blossoms are shown in various stages of maturity with the more mature and lighter-colored blossoms being displayed towards the top.
Figure 2:
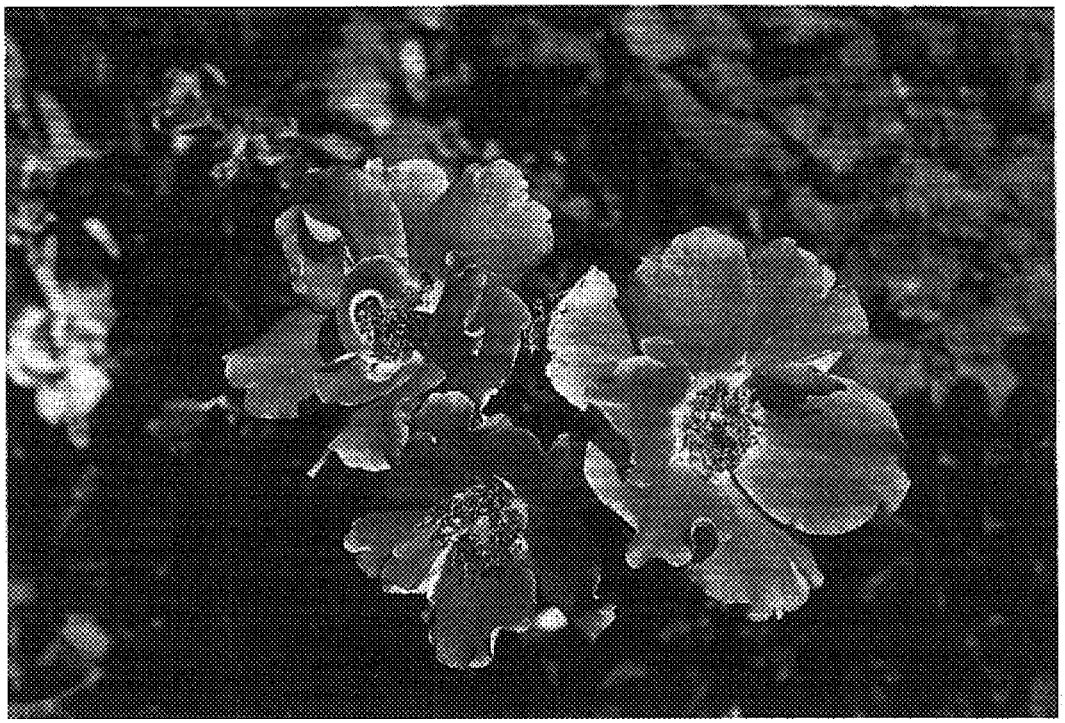
FIG. 2 illustrates a closer view of typical fully open blossoms of the new variety.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2002 at St. Paul, Minn., and May 2003 at Phoenix, Ariz.

Botanical classification: *Rosa hybrida,* var. 'BAIface'.
Class: Landscape Shrub.
Plant:
- *Height.*—Approximately 90 cm on average at the end of the growing season.
- *Width.*—Approximately 90 cm on average at the end of the growing season.
- *Habit.*—Compact, upright, bushy, and rounded.

Branches:
- *Color.*—Young stems: Yellow-Green Group 144B. Adult wood: Yellow-Green Group 146B and 146C.
- *Thorns.*—Size: commonly approximately 1 to 1.25 cm in length on average with some small bristles/prickles near the peduncle. Color: Yellow-Green Group 144B with highlights of Greyed-Purple Group 185B.

Leaves:
- *Stipules.*—Generally parallel with the auricle facing outward.
- *Petioles.*—Upper surface: Yellow-Green Group 146C. Under surface: Yellow-Green Group 146C suffused with Greyed-Purple Group 184B.
- *Leaflets.*—Number: 3, 5 (most often), and 7. Shape: ovate with a rounded base and an acuminate tip. Margin: serrulate. Texture: bears a satin finish and is physically firm. General appearance: medium green with a satin surface when mature. Color (young foliage): Upper surface: between Yellow-Green Group 146A and 146B with highlights of Red-Purple Group 59A near the margin. Under surface: Greyed-Purple Group 187B with highlights of Yellow-Green Group 146B near and including the main vein. Color (adult foliage): Upper surface: Green Group 138A. Under surface: Green Group 137C.

Inflorescence:
- *Number of flowers.*—Commonly approximately 3 blooms on average per cluster on a lateral stem.
- *Peduncle.*—Yellow-Green Group 146A with highlights of Greyed-Purple Group 184B in coloration, and the length is approximately 1.0 cm on average.
- *Sepals.*—Upper surface: Green Group 143C with streaks of Green Group 143A. Under surface: Green Group 143B with streaks of Green Group 143A and some pubescence. Size: approximately 1.75 cm in length on average.
- *Buds.*—Shape: generally oval to somewhat rectangular. Size: medium. Length: approximately 1.75 cm on average. Diameter: approximately 1.0 cm on average. Color: Upper petal surface: between Red-Purple Group 57A and 57B with a basal petal spot of Yellow Group 5A. Under petal surface: Red Group 53C lightening to Red Group 54C and 54D with a basal petal spot of Yellow Group 4A and a streak of Yellow Group 4C at the center.
- *Flower.*—Shape: semi-double. Diameter: approximately 8.75 cm on average. Color (when opening begins): Upper surface: Red-Purple Group 57A blended with Red-Purple Group 57B and 57C. Under surface: between Red-Purple Group 66B and Red-Purple Group 68D. Color (when blooming): Upper surface: between Red-Purple Group 66B and 66C blended with some Red Group 49C and near White Group 155D, as well as some Yellow Group 2C at the petal base and apex. Under surface: between Red Group 55B and 55C with highlights of Red-Purple Group 67A and Yellow Group 1D at the base. Color (at end of blooming): Upper surface: between Red-Purple Group 66B and 66C with fading to Red-Purple Group 68D, with Yellow Group 4D at the base, and White Group 155D at the apex. Under surface: Red Group 67A with highlights of Red-Purple Group 65C and 65D, and near Yellow Group 1D at the base. Color (basal petal spot): near Yellow Group 1D. Fragrance: slight spice. Lasting quality: the blossoms commonly last approximately 5 to 8 days on average depending upon the temperature and sunlight exposure. Petal number: approximately 11 under normal growing conditions. Petal shape: wedge-shaped with a curled apex and a ruffled edge. Petal drop: commonly the petals detach cleanly at full blossom maturity. Anthers: Yellow-Orange Group 17A. Filament number: commonly approximately 68 on average. Anther color: Yellow Group 13B. Filament color: Yellow Group 9B with highlights of Red Group 47B and 47C. Pistils: approximately 32 on average. Stigmas: Yellow-Green Group 12B in coloration. Styles: Yellow-Green Group 150B and Yellow-Green Group 154 in coloration. Receptacle: separate and free with achenes on the bottom and wall. Hip shape: ovoid. Hip length: approximately 2.0 cm. Hip width: approximately 1.75 cm. Seeds: dark brown in coloration, and approximately 4.5 mm in length.

Development:
- *Vegetation.*—Vigorous, and strong.
- *Blooming.*—In abundance in June and continuously for the remainder of the season.
- *Resistance to diseases.*—Excellent tolerance to Black Spot, and Powdery Mildew.
- *Hardiness zone.*—U.S.D.A. Hardiness Zone Nos. 4 to 9.

We claim:

1. A new and distinct variety of landscape shrub rose plant characterized by the following combination of characteristics:

(a) exhibits a compact, upright and bushy growth habit, (b) forms continuously in clusters attractive semi-double rich medium pink blossoms blended with rosy pink and white, (c) forms satiny medium green adult foliage, (d) displays excellent tolerance to Black Spot and Powdery Mildew; and (e) is particularly well suited for growing as attractive ornamentation in parks and gardens;

substantially as herein shown and described.

* * * * *